United States Patent [19]

Williams et al.

[11] Patent Number: 5,230,693

[45] Date of Patent: * Jul. 27, 1993

[54] IMPLANTABLE PROSTHETIC DEVICE FOR IMPLANTATION INTO A HUMAN PATIENT HAVING A SURFACE TREATED WITH MICROVASCULAR ENDOTHELIAL CELLS

[75] Inventors: Stuart K. Williams, Drexell; Bruce E. Jarrell, Philadelphia, both of Pa.

[73] Assignee: Thomas Jefferson University, Philadelphia, Pa.

[*] Notice: The portion of the term of this patent subsequent to Apr. 11, 2006 has been disclaimed.

[21] Appl. No.: 725,950

[22] Filed: Jun. 27, 1991

Related U.S. Application Data

[60] Continuation of Ser. No. 244,496, Sep. 12, 1988, abandoned, which is a division of Ser. No. 742,086, Jun. 6, 1985, Pat. No. 4,820,626.

[51] Int. Cl.$^5$ .......................... A61F 2/06; A61F 2/02; C12N 11/04; C12N 5/00
[52] U.S. Cl. ......................................... 600/36; 623/1; 435/1; 435/174; 435/182; 435/240.2
[58] Field of Search ........................ 435/1, 182, 240.2; 623/1; 600/36

[56] References Cited

U.S. PATENT DOCUMENTS 3,276,448  10/1966  Kronenthal ..................... 128/334

FOREIGN PATENT DOCUMENTS 0080956  6/1983  European Pat. Off. .
8303536  10/1983  PCT Int'l Appl. .
8401892  5/1984  PCT Int'l Appl. ................. 623/1

OTHER PUBLICATIONS

Stanley, et al. Enhanced Patency of Small-Diameter, Externally Supported Dacron, Iliofemoral Grafts Seeded with Endothelial Cells, Surgery vol. 92 No. 6 pp. 994–1005 Dec., 1982.
Kern, et al. Isolation and Culture of Microvascular Endothelium from Human Adipose Tissue, Journal of Clinical Investigation vol. 71 pp. 1822–1829 Jun., 1983.
Jarrell, et al. Human Adult Endothelial Cell Growth in Culture Journal of Vascular Surgery vol. 1 No. 6 pp. 757–764 Nov., 1984.
Jarrell, et al., Use of an Endothelial Monolayer on a Vascular Graft Prior to Implantation Annals of Surgery vol. 203 No. 6 pp. 671–678 Jun. 1986.
Radomski, et al. Initial Adherence of Human Capillary Endothelial Cells to Dacron, Journal of Surgical Research vol. 42 pp. 133–140 Feb., 1987.
Jarrell, et al. Use of Freshly Isolated Capillary Endothelial Cells for the Immediate Establishment of a Monolayer on a Vascular Graft at Surgery, Surgery vol. 100 No. 2 pp. 392–399 Aug., 1986.
Dilley, et al. Endothelial Seeding of Vascular Prostheses, in Biology of Endothelial Cells; Jaffe (Ed.) Martinus Nijhoff, Boston, 1984.
Burkel The Development of Cellular Linings in Artificial Vascular Prostheses in Biocompatible Polymers, Metals, and Composites. Szycher (Ed.) Technomic, Lancaster, U.S. 1983.

(List continued on next page.)

Primary Examiner—John J. Doll
Assistant Examiner—George C. Elliott
Attorney, Agent, or Firm—Woodcock, Washburn, Kurtz, Mackiewicz & Norris

[57] ABSTRACT

The present invention provides a synthetic or naturally occurring implant, such as a vascular graft, for implantation into a human patient. Uncultured, microvascular endothelial cells, isolated from microvascular endothelial cell rich tissue are disposed on at least one surface of the implant to provide at least about 50% confluence of the cells on the surface of the implant prior to implantation. In a preferred embodiment, the microvascular endothelial cells are obtained from fat tissue. Because of the large number of fresh microvascular endothelial cells that may be obtained from such tissue, sufficient cells may be placed on the implant so that they attach to provide at least 50% confluent coverage of the implant surface prior to the time of implantation.

14 Claims, 3 Drawing Sheets

OTHER PUBLICATIONS

Sharefkin, et al. Early Normalization of Platelet Survival by Endotheliat Seeding of Dacron Arterial Prostheses in Dogs Surgery vol. 92 No. 2 pp. 385-393 Aug., 1982.

Watkins, et al. Adult Human Saphendus Vein Endothelial Cells:Assessment of Their Reproductive Capacity for Use in Endothelial Seeding of Vascular Prostheses Journal of Surgical Research vol. 36, pp. 588-596 Jun., 1984.

Abedin, M. Z. et al., "Collagen Heterogeneity and its Functional Significance", *Die Angewandte Markromolekulare chemie*, vol. 111, No. 1701, Jan., 1983, pp. 107-122.

Herring et al., "A Single Staged Technique for Seeding Vascular Grafts with Autogenous Endothelium", *Surgery*, 1978, 84:498-504.

Graham et al., "Cultured Autogenous Endothelial Cell Seeding of Vascular Prosthetic Grafts", *Surg. Forum* 30:204-206 (1979).

Graham et al., "Expanded Polytetrafluoroethylene Vascular Prostheses Seeded With Enzymatically Derived and Cultured Canine Endothelial Cells", *Surgery* 91:550-559 (1982).

Berger et al., "Healing of Arterial Prostheses in Man" It's Incompleteness, *Ann. Surg.* 175:118-127 (1972).

Jaffe et al., "Synthesis of Antihemophilia Factor Antigen by Cultured Human Endothelial Cells", *J. Clin. Invest.* 55:2757-64 (1973).

Fishman, "Endothelium" A Distributed Organ of Diverse Capabilities, *Annals of New York Academy of Sciences*, pp. 1-8 (1982).

Sauvage et al., "Interspecies Healing of Porous Arterial Prostheses", *Arch Surg.* 109:698-705 (1974).

F. Hess et al., "The Endothelialization Process of a Fibrous Polyurethane Microvascular Prostheses After Implantation in the Abdominal Aorta of the Rat", *Journal of Cardiovascular Surgery*, vol. 24, No. 5, pp. 516-524 (Sep.-Oct. 1983).

W. K. Nichols et al., "Increased Adherence of Vascular Endothelial Cells to Biomer Precoated With Extracellular Matrix", *Trans. Am. Soc. Artif. Intern Organs*, 28:208-212 (1981).

C. L. Ives et al., "The Importance of Cell Origin and Substrate in the Kinetics of Endothelial Cell Alignment in Response to Steady Flow", *Trans. Am. Soc. Artif. Intern Organs*, 29:269-274 (1983).

S. G. Eskin et al., "Behavior of Endothelial Cells Cultured on Silastic and Dacron Velour Under Flow Conditions In Vitro: Implications for Prelining Vascular Grafts with Cells", *Artificial Organs*, 7(1):31-37 (1983).

T. A. Belden et al., "Endothelial Cell Seeding of Small-Diameter Vascular Grafts", *Trans. Am. Soc. Artif. Intern. Organs*, 28:173-177, (1982).

W. E. Burkel et al., "Fate of Knitted Dacron Velour Vascular Grafts Seeded with Enzymatically Derived Autologous Canine Endothelium", *Trans. Am. Soc. Artif. Intern. Organs*, 28:178-182 (1982).

M. B. Herring et al., "Seeding Arterial Prostheses with Vascular Endothelium" *Ann. Surg.*, vol. 190, No. 1, pp. 84-90 (Jul., 1979).

A. Wesolow, "The Healing of Arterial Prosthesis—The State of the Art", *Thorac. Cardiovasc. Surgeon*, 30:196-208 (1982).

T. Ishihara et al., "Occurrence and Significance of Endothelial Cells in Implanted Procine Bioprosthetic Valves", *American Journal of Cardiology*, 48:443-454 (Sep., 1981).

Williams et al., "Micropinocytic ingestion of glycosylated albumin by isolated microvessels: Possible role in pathogenesis of diabetic microangiopahty", *Proc. Natl. Acad. Sci. USA*, vol. 78, No. 4, pp. 2393-2397, Apr. 1981.

Williams et al., "Regulation of Micropinocytosis in Capillary Endothelium by Multivalent Cations", *Microvascular Research* 21, 175-182 (1981).

Williams et al., "Quantitative Determination of Deoxyribonuclein Acid from Cells Collected on Filters", *Analytical Biochemistry* 107:17-20 (1980).

Wagner et al., "Exclusion of Albumin from Vesicular Ingestion by Isolated Microvessels", *Microvascular Research* 19:127-130 (1980).

Williams et al., "Metabolic Studies on the Micropinocytic Process in Endothelial Cells", *Microvascular Research* 18:175-184 (1979).

Williams, "Vesicular Transport of Proteins by Capillary Endothelium", *Annals of the New York Academy of Sciences*, 457-467 (1983).

Williams et al., "Enhanced Vesicular Ingestion of Nonenzymatically Glucosylated Proteins by Capillary Endothelium", *Microvascular Research* 28:311-321 (1984).

Williams et al., "Endocytosis and Exocytosis of Protein in Capillary Endothelium", *Journal of Cellular Physiology*, 120:157-162 (1984).

OTHER PUBLICATIONS

Williams et al., "Isolation and Characterization of Brain Endothelial Cells: Morphology and Enzyme Activity", *Journal of Neurochemistry*, 35:374–381 (1980).

McDonagh et al., "The Preparation and Use of Fluorescent-Protein Conjugates for Microvascular Research", *Microvascular Research* 27:14–27 (1984).

Madri et al., "Capillary Endothelial Cell Cultures: Phenotypic Modulation by Matrix Components", *Journal of Cell Biology*, vol. 97, Jul., 1983, 153–165.

Williams et al., "Adult Human Endothelial Cell Compatability With Prosthetic Graft Material", *Journal of Surgical Research* 38:618–629 (1985).

van Wachem et al., "Interaction of Cultured Human Endothelial Cells with Polymeric Surfaces of Different Wettabilities", Biomaterials 6:403–408 (1985).

Azizkhan et al., "Mast Cell Heparin Stimulates Migration of Capillary Endothelial Cells in Vitro", *J. Exp. Med.*, vol. 152, Oct., 1980, pp. 931–944.

Roblin et al., "Cell Surface Changes Correlated with Density-Dependent Growth Inhibition". Glycosaminoglycan Metabolism in 3T3, SV3T3, and Con A Selected Revertant Cells, Biochemistry, vol. 14, No. 2, 1975, pp. 347–357.

Yang et al., "The Effect of Heparin on Growth of Mammalian Cells in Vitro (40290) *Proceedings of the Soc". for Experimental Biology and Medicine* 159:88–93 (1978).

Thornton et al., "Human Endothelial Cells: Use of Heparin in Cloning and Long-Term Serial Cultivation", *Science*, Nov. 11, 1983, vol. 222, pp. 623–625.

Laterra et al., "Functions for Fibronectin, Hyaluronate, and Heparan Proteoglycans in Substratum Adhesion of Fibroblasts", *Extracellular Matrix*, pp. 197–207, 1982.

Maciag et al., "Factors Which Stimulate the Growth of Human Umbilical Vein Endothelial Cells in Vitro", Jaffe, E. A. (ed.) Biology of endothelial cells. 1984, Martinus Nijhoff, pp. 87–140.

Madri, "The Immunochemistry of Extracellular Matrix", Boca Raton, Fla., CRC Press, (1982), vol. 1:75–90.

Baker et al., "Endothelialization of Human Collagen Surfaces with Human Adult Endothelial Cells", *American Journal of Surgery*, 150:197–200 (Aug., 1985).

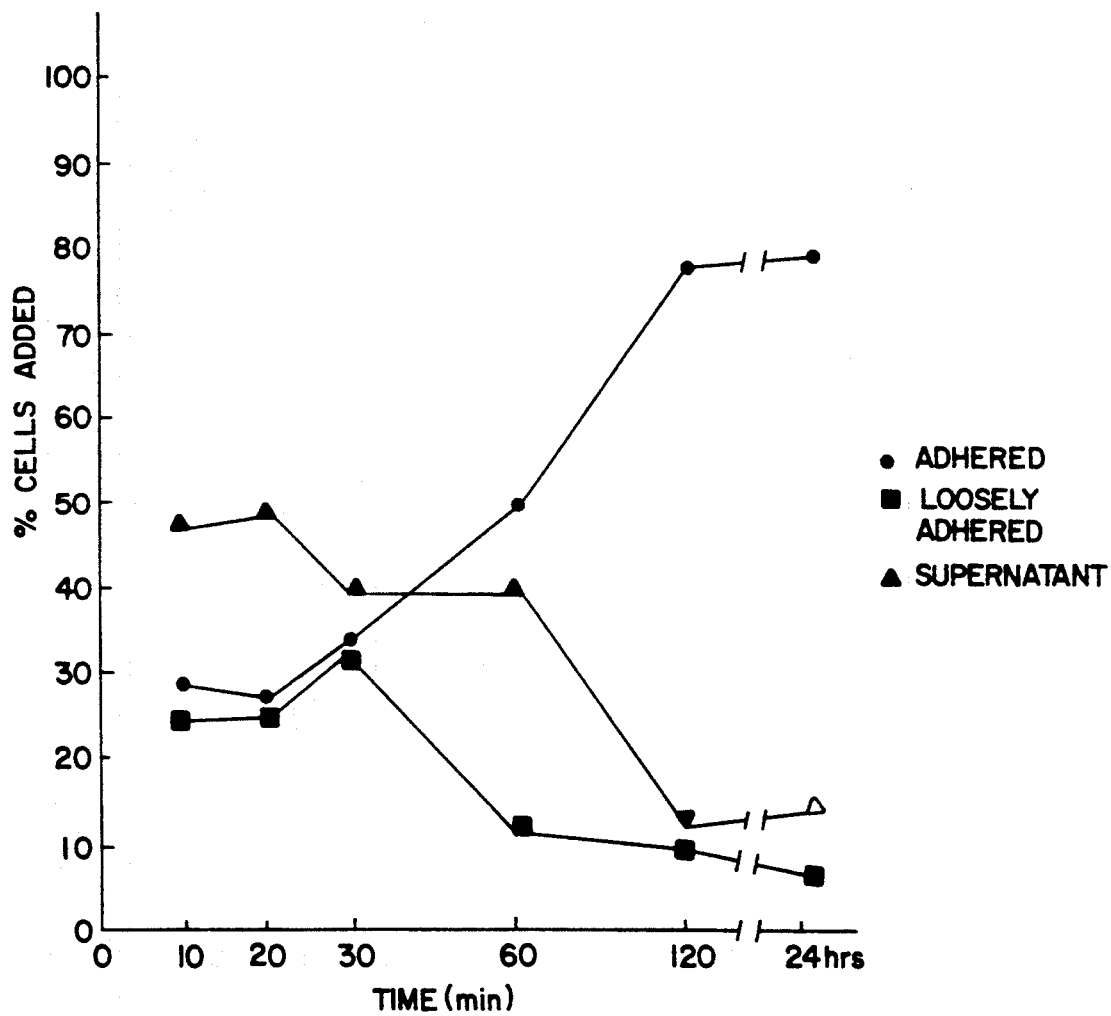

IMPLANTABLE PROSTHETIC DEVICE FOR IMPLANTATION INTO A HUMAN PATIENT HAVING A SURFACE TREATED WITH MICROVASCULAR ENDOTHELIAL CELLS

This is a continuation of application Ser. No. 244,496, filed Sep. 12, 1988 now abandoned, which is a division of application Ser. No. 742,086 filed Jun. 6, 1985, now U.S. Pat. No. 4,820,626 issued Apr. 11, 1989.

CROSS-REFERENCE TO RELATED APPLICATIONS

This application is related to U.S. Pat. No. 4,994,387, which issued on Feb. 19, 1991, from application Ser. No. 210,218, filed Jun. 17, 1988 which is a continuation of Ser. No. 099,241, filed Sep. 21, 1987 and now abandoned, which is a continuation of applications Ser. No. 848,913 and 848,917, both filed Apr. 7, 1986 and both now abandoned, which respectively, are continuations of applications Ser. No. 550,305, filed Nov. 10, 1983, a portion of which is assigned to the assignee hereof and which application is hereby incorporated by reference as if fully set forth herein, and 550,306, also filed Nov. 10, 1983, and now both abandoned.

BACKGROUND OF THE INVENTION

The present invention relates to the field of implantable prosthetic devices for implantation into humans, and more particularly to synthetic implants such as vascular grafts which are commonly used to replace the large veins or arteries of human patients.

The development of the idea of prosthetic vascular grafts has been a major goal of vascular surgery since the first grafts were used over 30 years ago. Most approaches have concentrated on creating a surface that is thromboresistant, with the majority of these efforts directed toward an improved polymer surface. Perhaps the ideal blood-surface interface is the naturally occurring human endothelium. If present on a prosthetic graft, it would offer many of the advantages of a native vessel. Unfortunately, endothelialization occurs only to a limited degree in prosthetic grafts when placed into humans, in contrast to animals where graft endothelialization does occur. Seeding endothelial cells onto preclotted prosthetic grafts prior to implantation has improved the endothelial cell coverage of grafts in animals, but this technique has had limited use in humans. See "Human Adult Endothelial Cell Growth in Culture", Bruce Jarrell et al, *Journal of Vascular Surgery*, Vol 1, No. 6, pp. 757-764 (November, 1984); Herring et al, "A Single and Staged Technique for Seeding Vascular Grafts with Autogenous Endothelium", *Surgery*, 1978, 84:498-504; Graham et al, "Cultured Autogenous Endothelial Cell Seeding of Vascular Prosthetic Grafts", *Surg Forum* 30:204-6 (1979); Graham et al, "Expanded Polytetrafluoroethylene Vascular Prostheses Seeded with Enzymatically Derived and Cultured Canine Endothelial Cells", *Surgery* 91:550-9 (1982) and Dilley et al, "Endothelial Seeding of Vascular Prostheses", Jaffe ed *Biology of Endothelial Cells*, The Hague: Martinus Nijhoff, 1984 pp 401-11.

Over the past three decades artificial grafts have been used to provide immediate restoration of blood flow to areas of ischemia as a result of atherosclerotic vascular disease. In addition, they have been used to provide vascular access for hemodialysis in patients with chronic renal failure, and in the repair of arterial aneurysms. Although initially successful at restoring perfusion to ischemic tissues, the long-term prognosis for these grafts is not encouraging. Over an extended period, grafts less than 4 mm in diameter lose their patency as they become occluded via fibrin deposition and cellular adhesion. Dilley supra. This process appears to be secondary, and to be due in part to the thrombogenic nature of the nude (i.e, non-endothelialized) surface of the implanted prostheses. See Berger et al, "Healing of Arterial Prostheses in Man: It's Incompleteness", *Ann. Surg.* 175:118-27 (1972). Thus, much current research is being aimed at either: (1) developing grafts with an artificial, non-thrombogenic surface, or (2) lining vascular prostheses with human endothelial cells, in the hope of producing a non-thrombogenic endothelial cell surface such as exists in native human vessels.

Endothelial cells from animal sources have been studied in culture since the 1920's. In 1973 Jaffe et al, successfully cultured endothelial cells from human umbilical veins and these cells have been characterized functionally. See Jaffe et al, "Synthesis of Antihemophilia Factor Antigen by Cultured Human Endothelial Cells", *J. Clin. Invest.* 55:2757-64 (1973); and Lewis, "Endothelium in Tissue Culture", *Am. J. Anat.* 30:39-59 (1922); Jaffe et al, "Culture of Human Endothelial Cells Derived From Umbilical Veins", *J. Clin. Invest.* 52:2745-56 (1973). These cell cultures demonstrate a growth potential, but the total number of cells produced from a single umbilical vein is usually quite limited, in the range of a 10-100-fold increase in harvested endothelial cells.

While several techniques have been proposed to increase the number of cells produced in the use of human umbilical vein endothelial cells, the ability to culture endothelial cells in large numbers remains less than ideal. Some investigators have had some success in culturing human adult endothelial cells from pulmonary arteries and veins, but only for short periods of time. It has also been shown that human iliac artery endothelial cells may be cultured for a short number of passages. In a study by Glassberg et al, for example, it is reported that 50 to 500 viable cells can be obtained per 5-inch vessel segment, a very low yield. "Cultured Endothelial Cells Derived From Human Iliac Arteries", *In Vitro* 18:859-66 (1982). Fry et al have reported successfully culturing human adult endothelial cells from abdominal arteries removed at the time of cadaver donor nephrectomy, but these cells also demonstrated early senescence.

It is apparent from existing techniques that it is difficult to produce enough cells to preendothelialize a graft with a reasonable amount of vessel from the donor patient. Rather than completely endothelializing a graft prior to implantation, the concept of subconfluent "seeding" of a preclotted graft developed. Seeding vascular grafts with autogenous endothelial cells has recently been shown to increase the rate of endothelial coverage of the grafts of experimental animals. See Herring et al and Graham et al supra. Once covered by endothelium, grafts in dogs have been shown to be less thrombogenic as measured by platelet re-activity, to be more resistant to inoculation from blood-born bacterial challenge, and to have prolonged patency of small-caliber vascular grafts. See Sharefkin et al, "Early Normalization of Platelet Survival by Endothelial Seeding of Dacron Arterial Prostheses in Dogs", *Surgery* 92:385-93 (1982); Stanley et al, "Enhanced Patency of Small Diameter Externally Supported Dacron Iliofemoral Grafts Seeded with Endothelial Cells", *Surgery* 92:994-1005 (1982); and Watkins et al, "Adult Human Saphenous Vein Endothelial Cells: Assessment of Their Reproductive Capacity for Use in Endothelial Seeding of Vascular Prostheses", *J. Surg. Res.* 36:588-96 (1984).

A point of major concern when translating to human graft seeding has been the ability to produce enough endothelial cells with the use of human vascular tissue to allow seeding at a density high enough to attain endothelial coverage of the graft. Watkins et al, using human saphenous vein remnants following coronary artery bypass surgery were able to produce small quantities of endothelial cells in culture, and reported a 100-fold increase in confluent cell area obtained in culture after 4 to 6 weeks. See Watkins et al supra.

Even if it were possible to substantially expand the number of endothelial cells available through vigorous culturing techniques, concerns would still remain concerning the "health" of these endothelial cells after as many as 40 or 50 population doublings. Furthermore, the incubation of such cells in cultures which are foreign to their natural environment raises further concerns about genetic alterations and/or patient contamination with viruses, toxins or other damaging materials.

Many endothelialization procedures are suggested in the literature. Investigations in this area have been complicated by the diverse nature of the endothelium itself, and by the species to species differences which have been found relating to the behavior and characteristics of the endothelium. Fishman "Endothelium: A Distributed Organ of Diverse Capabilities", *Annals of New York Academy of Sciences*, pp. 1-8 (1982); Sauvage et al, "Interspecies Healing of Porous Arterial Prostheses", *Arch Surg.* 109:698-705 (1974); and Berger, "Healing of Arterial Prostheses in Man: Its Incompleteness", supra. Nonetheless, the literature is replete with reports of experiments involving the seeding of endothelial cells on various grafts, in various species, with a mixture of results. F. Hess et al, "The Endothelialization Process of a Fibrous Polyurethane Microvascular Prostheses After Implantation in the Abdominal Aorta of the Rat", *Journal of Cardiovascular Surgery*, Vol. 24, No. 5, pp. 516-524 (September-October, 1983); W. K. Nicholas et al, "Increased Adherence of Vascular Endothelial Cells to Biomer Precoated with Extracelluar Matrix", *Trans. Am. Soc. Artif. Intern Organs*, 28:208-212 (1981); C.L. Ives et al, "The Importance of Cell Origin and Substrate in the Kinetics of Endothelial cell Alignment in Response to Steady v Flow", *Trans. Am. Soc. Artif. Inten Organs*, 29:269-274 (1983); L. M. Graham et al, "Expanded Polytetrafluoroethylene Vascular Prostheses Seeded with Enzymatically Derived and Cultured Canine Endothelial Cells", *Surgery*, Vol 91, No. 5, pp. 550-559 (1982); S. G. Eskin et al, "Behavior of Endothelial Cells Cultured on Silastic and Dacron Velour Under Flow Conditions In Vitro: Implications for Prelining Vascular Grafts with Cells", *Artificial Organs*, 7(1):31-37 (1983);T.A. Belden et al, "Endothelial Cell Seeding of Small-Diameter Vascular Grafts", *Trans. Am. Soc. Artif. Intern. Organs*, 28:173-177, (1982); W.E. Burkel et al, "Fate of Knitted Dacron Velour Vascular Grafts Seeded with Enzymatically Derived Autologous Canine Endothelium", *Trans. Am. Soc. Artif. Intern. Organs*, 28:178-182 (1982); M.T. Watkins et al, "Adult Human Saphenous Vein Endothelial Cells: Assessment of Their Reproductive Capacity for Use in Endothelial Seeding of Vascular Prostheses", *Journal of Surgical Research*, 36:588-596 (1984); M. B. Herring et al, "Seeding Arterial Prostheses with Vascular Endothelium", *Ann. Surg.*, Vol. 190, No. 1, pp. 84-90 (July, 1979); A. Wesolow, "The Healing of Arterial Prostheses—The State of the Art", *Thorac. Cardiovasc. Surgeon*, 30:196-208 (1982); T. Ishihara et al, "Occurrence and Significance of Endothelial Cells in Implanted Porcine Bioprosthetic Valves", *American Journal of Cardiology*, 48:443-454 (September, 1981); W. E. Burkel et al, "Fate of Knitted Dacron Velour Vascular Grafts Seeded with Enzymatically Derived Autologous Canine Endothelium", *Trans. Am. Soc. Artif Intern Organ*, 28:178-182 (1982).

Notwithstanding the work reported in this field, a need still exists for a simple reliable procedure which can successfully endothelialize the surfaces of human implants, such as the surfaces of vascular grafts.

SUMMARY OF THE INVENTION

This invention provides a novel method for treating a synthetic or naturally occurring implant intended for implantation in a human patient, comprising the steps of obtaining human microvascular endothelial cell rich tissue from that patient; separating microvascular endothelial cells from that tissue; and applying said microvascular endothelial cells onto said implant to provide at least about 50% or greater confluence of said cells on the surface of said implant to be treated.

Applicants have recognized that human microvascular endothelial cells, that is, the cells which are derived from capillaries, arterioles, and venules, will function suitably in place of large vessel cells even though there are morphological and functional differences between large vessel endothelial cells and microvascular endothelial cells in their native tissues. Moreover, microvascular endothelial cells are present in an abundant supply in body tissue, most notably in fat tissue, and may be used to establish a degree of preimplantation confluence (i.e., at least 50% confluence) which should dramatically improve the prognosis of most implants. For purposes of further description, fat tissue is designated as the source of endothelial cells, but it is to be recognized that endothelial cells from other tissue sources may be used as well.

A vascular graft or other implant is treated to confluence using microvascular endothelial cells which are separated from fat which is obtained at the beginning of an uninterrupted surgical procedure. Fat tissue is removed from the patient after sterile conditions have been established. Microvascular endothelial cells in that fat are then quickly separated from their related tissue by enzymatic digestion and centrifugation, and are used to treat a surface which is then implanted in the patient during the latter stages of the same operation. This procedure obviates any need to culture adult endothelial cells to increase their numbers, and permits a patient to receive a graft which has been treated up to or above confluence with his own fresh, "healthy" endothelial cells.

In accordance with the preferred embodiment of the present invention, the microvascular rich tissue obtained is perinephric fat, subcutaneous fat, omentum, or fat associated with the thoracic or peritoneal cavity. This tissue is then subjected to digestion using a proteolytic enzyme, such as a collagenase comprising caseanase and trypsin, which is incubated with the tissue until the tissue mass disperses to produce a tissue digest. The microvascular endothelial cells are then separated from the digest using low speed centrifugation to produce an endothelial cell rich pellet. The pellet is washed with a buffered saline solution, and may be further purified using a continuous gradient centrifugation process or by use of selective sieving. The resulting microvascular endothelial cells are then preferably suspended in a buffered saline solution containing plasma protein, preferably about 1% plasma protein. This suspension, which comprises, on a volumetric basis, a pellet to solution ratio of 1:5 to 1:15, or preferably about 1:10, is then used to treat the surface by incubating cells with that surface until sufficient adherence of the microvascular endothelial cells to that surface occurs to provide at least 50% confluence. The surface may also be treated by mixing endothelial cells with blood, plasma, or some other gel forming solution such as collagens, adding the cell-solution mixture to the surface and allowing a clot to form. As a result, an improved graft or implant is provided having endothelialized surfaces which are either confluent, or which will reach confluence quite rapidly (within one population doubling) following implantation.

Accordingly, a primary object of the present invention is the provision of a process for improving endothelial cell coverage of vascular grafts and other implants.

A further object of the present invention is the provision of an improved synthetic or naturally occurring implant or graft, particularly an improved vascular graft, which is endothelialized with microvascular endothelial cells.

These and other objects of the present invention will become apparent from the following, more detailed description.

BRIEF DESCRIPTION OF THE DRAWINGS

FIGS. 2A and 2B are graphs illustrating the adherence of thymidine labelled human adult endothelial cells (HAEC) to untreated (FIG. 2A) and platelet rich plasma treated (FIG. 2B) Dacron polyester grafts over a period of 24 hours from the time of seeding.

DESCRIPTION OF THE PREFERRED EMBODIMENT

Figure 1:
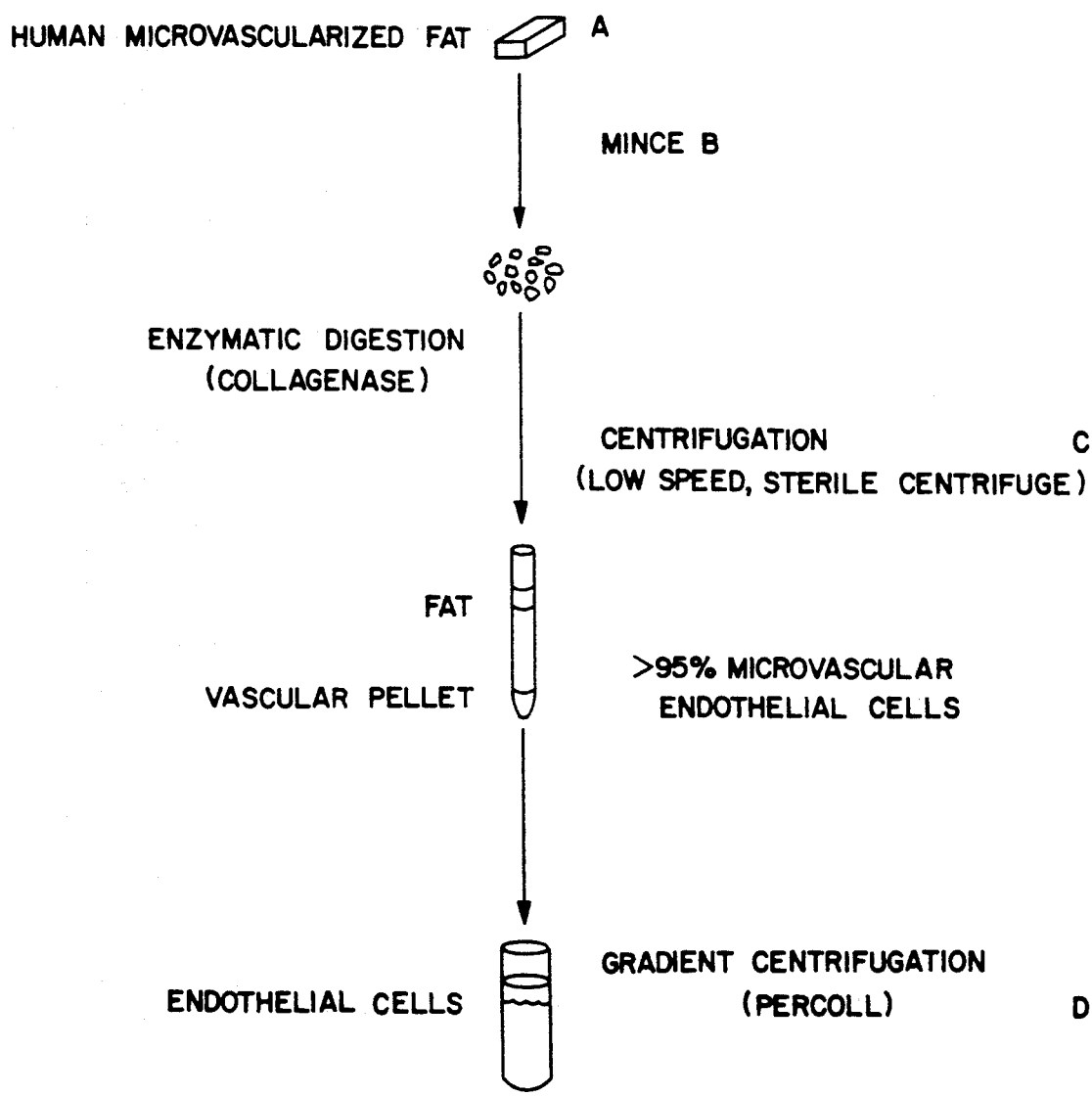
FIG. 1 is a diagram representing the steps followed to obtain human microvascular endothelial cells for use in accordance with the present invention.
Figure 2B:
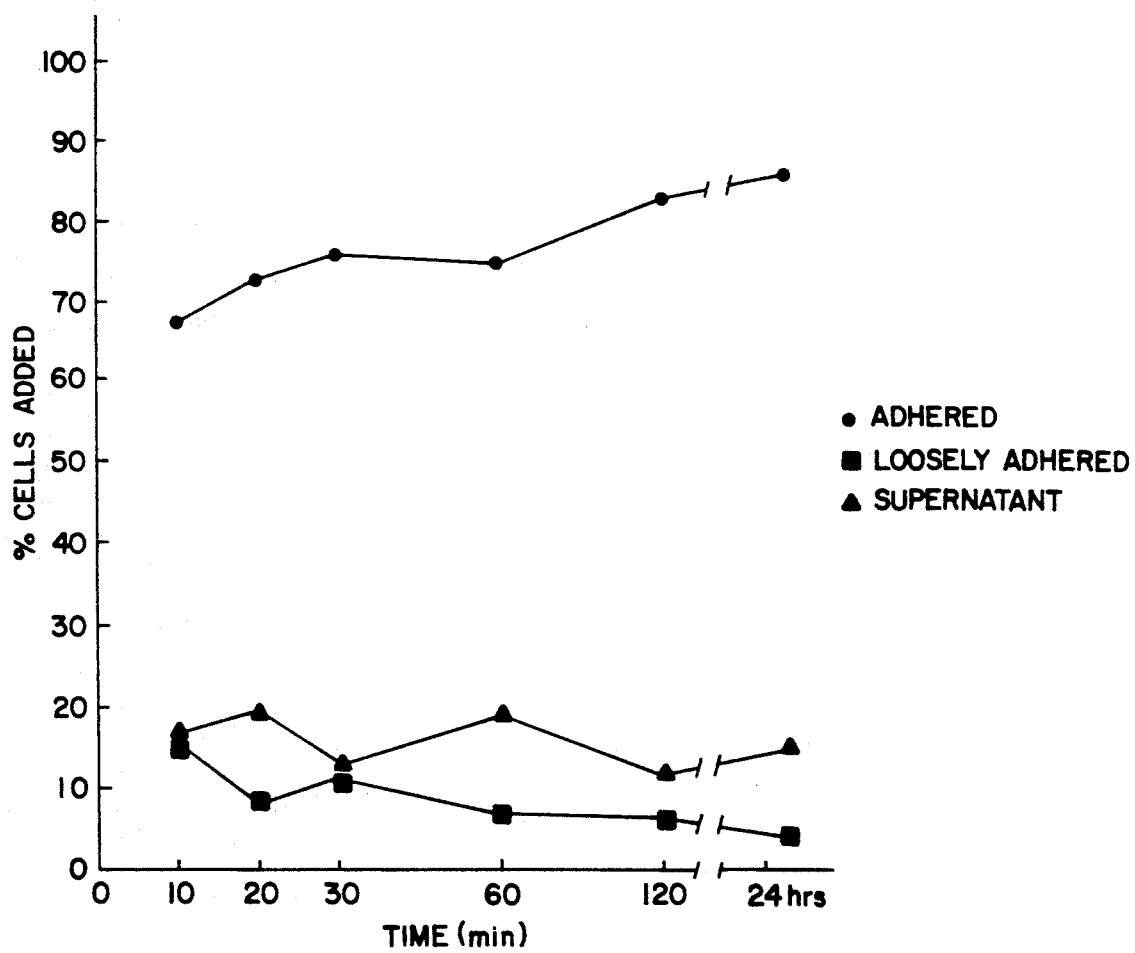

The preferred method of the present invention stems from work to investigate the function and characteristics of different types of endothelial cells. The method described herein permits the isolation of large quantities of microvascular endothelial cells from human microvascularized tissue (perinephric fat, omentum, or subcutaneous fat) under sterile conditions (e.g., the operating room). Procurement of large quantities of cells does not require tissue culturing subsequent to their isolation. These procedures are related to those developed during investigations concerning the isolation of non-human (rat) microvessel endothelial cells using rat epididymal fat as a source of tissue. The methods for isolation of non-human rat fat microvessel endothelial cells have recently been reported as being useful for the isolation and culture of human microvascular endothelial cells from skin and fat. Kern et al report that these isolated endothelial cells may subsequently be cultured and used in functional studies. *J. Clin. Invest.* 71:1822-1829 (1983). See also Jarrell et al, "Human Adult Endothelial Cell Growth In Culture", *Journal of Vascular Surgery* 1(6):757-764 (November, 1984) which is hereby incorporated by reference.

The present invention provides a novel method of using isolated microvascular endothelial cells for producing an endothelial cell lining on intravascular implants. Such implants include but are not limited to, for example, intravascular devices such as artificial vascular prostheses, artificial hearts, and heart valves. It is anticipated that the herein described procedures may lead to the development of other artificial organs or devices. These organs and devices will receive circulating blood either following implantation or in an extracorporeal circuit, and the present procedures provide a non-thrombogenic or anti-thrombogenic interface between the blood and the implanted surface. The immediate objective of the present invention is the use of the herein disclosed methods for endothelializing surfaces composed of known synthetic materials, such as polyester and polytetrafluoroethylene, or naturally occurring materials, such as an umbilical vein, saphenous vein, and native bovine artery.

The present invention provides a method of treating an implant intended for implantation in a human patient comprising: obtaining human microvascular rich tissue from that patient; separating microvascular endothelial cells from that tissue; and placing said microvascular endothelial cells onto said implant to provide at least about fifty percent (50%) confluence of said cells on the surface of said implant to be treated. This method is quick and relatively simple, and facilitates the implantation of a prosthesis or surface which has been treated with the patient's own "fresh" (uncultured) endothelial cells. Since the entire surgical procedure may be performed in its entirety in a single sterile environment, the likelihood of contaminating the endothelialized graft is minimized.

The method of the present invention provides for the isolation of large quantities of endothelial cells without the need for tissue culturing. Yet, the procedures involved may be readily performed in an operating room. A general flow diagram of the procedure for separating microvascular endothelial cells from a patient's tissue is illustrated in FIG. 1. While these procedures may also be used for the isolation of endothelial cells from tissues other than fat, such as brain, lung, retina, adrenal glands, liver and muscle, the use of fat tissue as the source for the cells is preferred due to its abundance and availability, and due to the fact that its removal should not adversely affect the patient being treated. Accordingly, as shown in FIG. 1, an amount of human microvascularized fat (A) may be procured from a number of sources. Although less preferred, it is possible to obtain human perinephric fat from brain-dead but heart-beating cadaver donors, or from donors other than the patient during the donor's surgery. In any event, the donated tissue is then immediately transferred to ice cold buffered saline (pH 7.4) wherein the buffering agent is preferably a phosphate, i.e., a phosphate buffered saline (PBS). The tissue is minced (Step B) with fine scissors and the buffer decanted. The proteolytic enzyme collagenase, containing caseanase and trypsin, is added to the tissue and incubated at 37° C. until the tissue mass disperses. This digestion occurs within thirty (30) minutes, and generally should be less than fifteen (15) minutes. The digest is transferred to a sterile test tube and centrifuged (Step C) at low speed (700× g) in a table top centrifuge for five (5) minutes at room temperature. The pellet of cells thus formed consists of greater than ninety-five percent (95%) endothelial cells. These endothelial cells are described herein as microvascular endothelial cells (MEC) since they originate from the arterioles, capillaries and venules, all elements of the microvasculature. This MEC pellet is washed one time by centrifugation with buffered saline, preferably PBS, and can be used directly without further purification in the treatment (application) step described herein.

Alternatively, these microvascular endothelial cells may be further purified by centrifuging the cells with a continuous gradient (Step D of FIG. 1). This gradient can be formed from a number of large molecular weight solutes, including albumin, dextran, or commercially available density gradient materials, such as Percoll (Pharmacia Inc.) or Nycodenz (Nyegaard and Company, Norway). Gradient centrifugation is used to remove red cells, white cells and smooth muscle cells. A forty-five percent (45%) solution of Percoll has routinely been used in the studies reported herein. Cells are layered on the surface of the Percoll solution and centrifuged at 13,000× g for twenty (20) minutes. A thick band of endothelial cells results at the upper end of the gradient. These cells are removed with a pipette and washed one time by centrifugation with phosphate-buffered saline.

The microvascular endothelial cells derived from human microvascularized tissue may then be used directly in the seeding step of the present invention without further treatment or culturing for the application to vascular prosthetic surfaces. A major advantage of this procedure is the procurement of large quantities of endothelial cells from human tissue for the coating of vascular grafts. In addition, these cells can be obtained from the donor who will receive the prosthetic implant. This methodology thus permits treatment of implantable surfaces with autologous endothelial cells.

In accordance with the method of the present invention, the prosthetic surfaces to be treated can be placed directly, without any pretreatment, in the condition in which they are packaged by the manufacturers for direct implantation into patients. Alternatively, the prosthetic surface can be pretreated with a protein or protein-like solution. Pretreatment is used to accelerate the adherence, spreading and growth of endothelial cells on the surface.

In performing the treatment step of the present invention, isolated human microvascular endothelial cells are suspended in a buffered saline which contains plasma-derived protein from the patient. This protein solution is prepared by mixing six parts buffered solution with one part plasma to produce a solution which contains approximately one percent (1%) protein. The data set forth in Table 1 indicates that endothelial attachment is affected by protein concentration in the suspension. As the data in Table 1 illustrates, the optimum protein concentration is about one percent (1%), and indicates the need for protein during surface treatment. Albumin is the preferred source of the protein, but non-plasma sources of protein can be used.

TABLE I

Effects of Varying Albumin Concentrations On The Initial Adherence and Growth of HAEC.

| ALBUMIN CONCENTRATION | PERCENTAGE OF CONFLUENCE+ TIME | |
| --- | --- | --- |
|  | 2 HOURS | 24 HOURS |
| 0% | 36.5% | 63.6%* |
| 0.1% | 32.5% | 61.2%* |
| 1.0% | 47.7% | 67.9%* |

TABLE I-continued

Effects of Varying Albumin Concentrations On The Initial Adherence and Growth of HAEC.

| ALBUMIN CONCENTRATION | PERCENTAGE OF CONFLUENCE+ TIME | |
| --- | --- | --- |
|  | 2 HOURS | 24 HOURS |
| 4.5% | 11.5% | 61.7%* |

+($\#EC/10^5$ cells/cm$^2$)
*Significant Change

The microvascularized endothelial cell suspension is then preferably pelletized by centrifugation (200× g) and the pellet resuspended with protein-containing buffer solution. This resuspension should be performed at a ratio of approximately 1:5 to 1:15 or about 1:10 volumes of packed microvascular endothelial cells to buffer solution. The cell suspension is added to tubular grafts and the ends clamped, or the cells are layered upon the surface to be treated. Optimum periods for cell interaction have not yet been defined with precision, and are expected to vary depending upon the material of the prostheses, the nature of any pretreatments it may have received and whether the surface of the prostheses has been modified to improve its acceptance of the microvascular endothelial cells. It has been found that the adherence of endothelial cells requires two hours on an untreated polyester graft surface, and less than ten minutes on similar surfaces pretreated with protein. This adhesion behavior has been confirmed by scanning electron micrographs of human microvessel endothelial cells (MEC) on plain, untreated Dacron grafts. Following incubation for a sufficient time to permit adherence of the endothelial cells with the graft surface, the surface is washed with a protein containing buffer. The prosthesis can now be implanted in its normal manner.

It has been found, based on both biochemical data and morphological data, that human microvascular endothelial cells will adhere to untreated graft surfaces. Scanning electron micrographs show that human MEC placed onto untreated Dacron polyester using procedures described above will result in adherence, followed by cell coverage (complete confluence) following one day in culture. The cells attach to specific areas on the graft and do not exhibit complete coverage of untreated graft surfaces. When human MEC are seeded onto plasma-treated Dacron polyester grafts, the coverage is much greater initially as compared to untreated Dacron surfaces. Scanning electron micrographs illustrate near confluent coverage of plasma coated grafts with human MEC. Table 2 illustrates the adherence and growth of human microvessel endothelial cells on untreated and protein-coated Dacron polyester grafts, initially at day 1, and after fourteen (14) days.

TABLE 2

Adherence and growth of human microvessel endothelial cells On untreated and protein coated Dacron grafts.

| DACRON PRETREATMENT TIME (DAYS) | PERCENTAGE OF CONFLUENCE+ | | | | | |
| --- | --- | --- | --- | --- | --- | --- |
|  | EC-0 | | EC-2 | | EC-10 | |
|  | 1 | 14 | 1 | 14 | 1 | 14 |
| UNTREATED | 37% | 37% | 43% | 56%* | 44% | 38% |
| COLLAGEN | 29% | 31% | 59% | 68% | 47% | 26% |
| COLLAGEN AND PLASMA | 34% | 44% | 47% | 76%* | 66% | 39%* |
| PLASMA | 53% | 55% | 65% | 100%* | 63% | 35%* |

+(# $EC/10^5$ cells/cm$^2$)
*SIGNIFICANT CHANGE

As Table 2 indicates, MEC adherence is facilitated by protein treatment of graft surfaces. It has also been found that the endothelial cell proliferation on prosthetic surfaces is stimulated by the presence of protein treatment.

The creation of a confluent layer of endothelial cells on prosthetic surfaces is dependent on two major variables. First, the initial adherence of cells must be maximized to provide at least about fifty percent (50%) initial surface coverage. Procurement of large vessel endothelial cells to provide at least about fifty percent (50%) coverage is extremely difficult, if not impossible, since the only available source of cells is the patient's own large vessels. Although large vessel cells can be isolated and cultured to provide a large number of cells, the obvious problems associated with tissue culture media would then be presented. Microvascularized fat provides a rich source of endothelial cells for seeding. Twenty grams of the patient's fat will provide ample endothelial cells to seed a surface area of one hundred and eighty square centimeters (180 $cm^2$), the surface area represented by a typical femoral artery to popliteal artery bypass graft.

A second variable to be considered is the ability of endothelial cells to proliferate (grow) on a prosthetic surface. Application at fifty percent (50%) confluence requires the cells to duplicate one time to create a confluent cell layer. Table 2 shows that on the preferred protein coated surface (coated with platelet rich plasma), the cells will duplicate at least once in tissue culture media which contains growth factor. In the body, however, these growth factors would presumably not be present, and therefore, the ability to treat surfaces at or in excess of confluence is advantageous. Again, the availability of human MEC in large quantities permits the application of endothelial cells on a surface at densities capable of establishing a confluent monolayer or near confluent monolayer at the time of implantation.

The application of human endothelial cells on prosthetic surfaces may be performed onto protein surfaces, as mentioned above, or upon surfaces which have been modified to emulate protein surfaces. Such modified surfaces are well-known to the endothelial cell tissue culture art. Alternatively, the endothelial cells may be "preclotted" into a fibrin (protein) gel which forms within and around the graft. Data indicate that human microvascular endothelial cells can be gelled within a protein meshwork, and following incubation in culture media, will migrate to the surface of the gel. This has been confirmed from scanning electron micrographs which show human microvascular endothelial cells forming a confluent monolayer on the surface of a Dacron polyester graft after these cells were preclotted in human plasma.

The dog model has been used to confirm on nonhuman subjects the feasibility of seeding grafts with microvessel endothelial cells. Dog microvessels were isolated from perinephric fat and seeded onto grafts according to the procedures described above. The grafts were implanted in the carotid artery and examined by scanning electron microscopy after two (2) days. Areas of confluent endothelial monolayers were observed.

"Dacron" is a trademark of E.I. duPont de Nemours and Company of Wilmington, Del., which is used to identify a particular polyethylene terephthalate polyester which is a condensation product of methyl terephthalate and ethylene glycol. Those of ordinary skill in the art will further recognize that various departures can be made from the methods and procedures described herein without departing from the scope of the present invention, which is defined more particularly in the claims appended hereto.

What is claimed is:

1. An implant for implantation into a human patient, having disposed on at least one surface thereof uncultured human microvascular endothelial cells obtained from human microvascular endothelial cell rich tissue, wherein said uncultured cells are at least about 50% confluent on the surface of said implant prior to the time of implantation.

2. The implant of claim 1 wherein said uncultured cells are adhered to said surface prior to implantation.

3. The implant of claim 1 wherein said implant is a vascular graft.

4. The implant of claim 3 wherein said vascular graft is a polyester graft.

5. The implant of claim 4 wherein said polyester is a condensation product of methyl terephthalate and ethylene glycol.

6. The implant of claim 4 wherein said polyester has been surface modified to emulate protein.

7. The implant of claim 1 wherein said implant comprises a polyester surface coated with plasma protein and with uncultured human microvascular endothelial cells.

8. The implant of claim 1 wherein said uncultured human microvascular endothelial cells are preclotted in a protein gel.

9. The implant of claim 8 where said protein gel is a fibrin gel.

10. The implant of claim 1 wherein said uncultured human microvascular endothelial cells are preclotted in human plasma.

11. The implant of claim 1 wherein said human microvascular endothelial cell rich tissue is fat tissue.

12. The implant of claim 11 wherein said tissue is selected from the group consisting of fat associated with the thoracic or peritoneal cavities, perinephric fat and subcutaneous fat.

13. The implant of claim 1 wherein said tissue is omentum.

14. An implant for implantation into a human patient, having disposed on at least one surface thereof uncultured human microvascular cells obtained from human microvascular endothelial cell rich tissue from that patient, wherein said uncultured cells are applied onto said implant to provide at least about 50% confluence on the surface of said implant prior to the time of implantation.

* * * * *